United States Patent [19]
Guarnieri et al.

[11] Patent Number: 6,127,417
[45] Date of Patent: Oct. 3, 2000

[54] STABLE DERIVATIVES OF UBIQUINOLE, PROCESSES FOR THEIR PRODUCTION AND PHARMACEUTICAL USE THEREOF

[75] Inventors: Decimo Guarnieri, Pomezia Rome; Santo Carbone, Latina; Siro Passi, Rome, all of Italy

[73] Assignee: IDI Farmaceutici S.p.A., Rome, Italy

[21] Appl. No.: 09/230,266

[22] PCT Filed: Jul. 23, 1997

[86] PCT No.: PCT/IT97/00184

§ 371 Date: Aug. 3, 1999

§ 102(e) Date: Aug. 3, 1999

[87] PCT Pub. No.: WO98/04512

PCT Pub. Date: Feb. 5, 1998

[30] Foreign Application Priority Data

Jul. 26, 1996 [IT] Italy .................................. RM96A0529

[51] Int. Cl.$^7$ ............................. A01N 37/02; A01N 37/08
[52] U.S. Cl. ......................... 514/548; 514/546; 514/553; 514/576; 514/720
[58] Field of Search .................................... 514/553, 576, 514/546, 548, 720

[56] References Cited

U.S. PATENT DOCUMENTS 3,068,295   12/1962   Folkers et al. .

FOREIGN PATENT DOCUMENTS 2 258 520   8/1973   Germany .
952581      5/1963   United Kingdom .

*Primary Examiner*—Deborah Carr
*Attorney, Agent, or Firm*—Browdy and Neimark

[57] ABSTRACT

New stable derivatives of ubiquinole are described, having general formula (I), along with processes for their production and their pharmaceutical use, in particular in the treatment of intracellular oxidative stress and diseases involving oxidative stress of this kind.

20 Claims, 5 Drawing Sheets

UBIQUINOLE DIACETATE

UBIQUINOLE DIACETATE

UBIQUINOLE DIPROPIONATE

UBIQUINOLE DIBUTYRATE

UBIQUINOLE DIMETHYLETHER

UBIQUINOLE DIETHYLETHER

STABLE DERIVATIVES OF UBIQUINOLE, PROCESSES FOR THEIR PRODUCTION AND PHARMACEUTICAL USE THEREOF

This application is a 571 of PCT/IT97/00184 filed Jul. 23, 1997.

TECHNICAL FIELD

The present invention relates to stable derivatives of ubiquinole, processes for their Production and the pharmaceutical use thereof.

BACKGROUND ART

Ubiquinone, (2,3-dimethoxy-5-methyl-6-decaprenylbenzoquinone) or coenzyme $Q_{10}$ ($CoQ_{10}$) is a quinone of lipidic nature, an essential redox component of the mitochondrial respiratory chain, where it acts as an electron shuttle, controlling the efficiency of oxidative phophorylation. Ubiquinone also exerts another important biological function, acting as an antioxidant for cell membranes, in harmony and in synergism with Vitamin E. Recent studies (Takahashi T., et al., (1993) Lipids 28, 803–809; Aberg F., et al., (1992) Arch-Biophys. 295, 230–234) have demonstrated that in certain human and animal test tissues (liver, heart, kidney, pancreas, etc.) the levels of ubiquinone ($CoQ_{10}$), especially in its reduced form, known as ubiquinole ($CoQ_{10}H_2$) are higher than those of Vitamin E.

The following reaction scheme shows the balance between the oxidised and reduced forms.

| Tissue | Content μg/g tissue | $CoQ_{10}H_2$ (%) |
|---|---|---|
| heart | 114.0 | 61 |
| kidney | 66.5 | 75 |
| liver | 54.9 | 95 |
| muscle | 39.7 | 65 |
| pancreas | 32.7 | 100 |
| thyroid | 24.7 | 70 |
| spleen | 24.6 | 85 |
| brain | 13.4 | 23 |
| intestine | 11.5 | 93 |
| colon | 10.7 | 87 |
| testicle | 10.5 | 85 |
| lung | 7.9 | 25 |

This study demonstrates that the reduced form ubiquinole almost always prevails over the oxidised form, to the extent that, in the pancreas, it is practically the only form present.

The above has been demonstrated in the case of healthy aerobic organisms, that is to say when the ubiquinole prevails over the ubiquinone and when, as demonstrated in scientific literature (Ernster L., et al. (1993) The Clinical Invest. 71, 60–65; Frei B., et al., (1990) Medical Sciences 87, 4879–4883; Hauska G. et al., (1983) Biochim. Biophys. Acta 726, 97–133; Kroger A. et al., (1973) European J. Biochem 24, 358–368) the quinone-reductases are practically inextinguishable.

However, it has been found that in conditions of continuous (or high) intracellular oxidative stress, for example in diseases connected with ageing or in the case of acquired

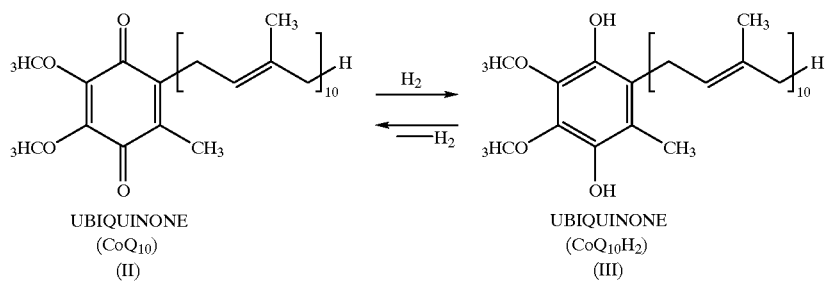

UBIQUINONE
($CoQ_{10}$)
(II)

UBIQUINONE
($CoQ_{10}H_2$)
(III)

Ubiquinone, especially in its reduced form ubiquinole, appears to have a higher effectiveness than Vitamin E in inhibiting lipidic peroxidation of membranes; this function of ubiquinone is explicated in a different site (the central level of the lipidic bi-layer) from that in which Vitamin E acts (close to the surface of the bi-layer). Ubiquinole would appear to form in the tissues following the reduction of ubiquinone or the co-enzyme Q semiquinone ($CoQ_{10}H$) by the enzymatic systems present in the membranes and generally indicated as quinone-reductases (NAD (P) H-dependent electron carriers), which are theoretically inextinguishable in perfectly functional aerobic organisms.

Aberg et al. (cited work) have determined the ubiquinole content as a percentage ratio of ubiquinone, in human tissues, as indicated in the following table.

immuno-deficiency syndrome (AIDS), the enzymatic electron carrier systems lose their ability to perform their biological reducing function properly, or entirely, and this causes a drop in the ubiquinole levels in tissues. Furthermore, in the case of the diseases mentioned above, the reduced endogenous synthesis of ubiquinone is another factor that causes a drop in the levels of ubiquinole in tissues.

There was therefore a problem in the state of the art relating to how, in cases of intracellular oxidative stress, to restore the levels of ubiquinole in tissues to levels close to or equivalent to those found in a healthy organism. The proposed pharmacological solution consisted in the administration of ubiquinone of exogenous origin. However, this solution created a problem of low efficiency, as the quinone-reductases, that is to say the enzymes capable of reducing ubiquinone to ubiquinole, although theoretically inextinguishable in a healthy organism, become incapable of performing their function correctly in case of a sick organism, particularly in the presence of continuous or high intracellular oxidative stress.

As a result of this, even administration of large amounts of ubiquinone were unable to give a consistent rise in the levels of ubiquinole present in tissues. On the other hand, direct administration of ubiquinole was not possible, due to the instability of the molecule, which decomposes into ubiquinone and semiquinone as soon as it is synthesised. Just the knowledge of the instability of the ubiquinole molecule has led one to assume up to now that the direct administration of ubiquinole was impracticable, a fact further confirmed by the absence in the state of the art of documents having as their object the administration of ubiquinole itself or in the form of derivatives.

DISCLOSURE OF THE INVENTION

It has now surprisingly been found that the level of ubiquinole in tissues, that are in conditions of continuous or high oxidative stress, can be reintegrated to the level of healthy organisms by administering stable derivatives of ubiquinole that are transformed into ubiquinole within the organism.

Object of the present invention are therefore compounds of formula I

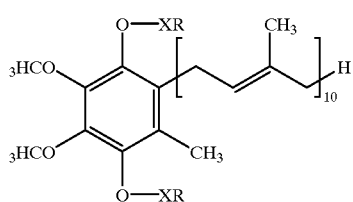

in which R is a linear or branched alkyl group with a number of carbon atoms from 1 to 20, or an aryl group optionally substituted with alkyl with from 1 to 6 carbon atoms, and X is absent or a CO group.

BRIEF DESCRIPTION OF DRAWINGS

Enclosed with the present description are five figures, in which.

Figure 1:
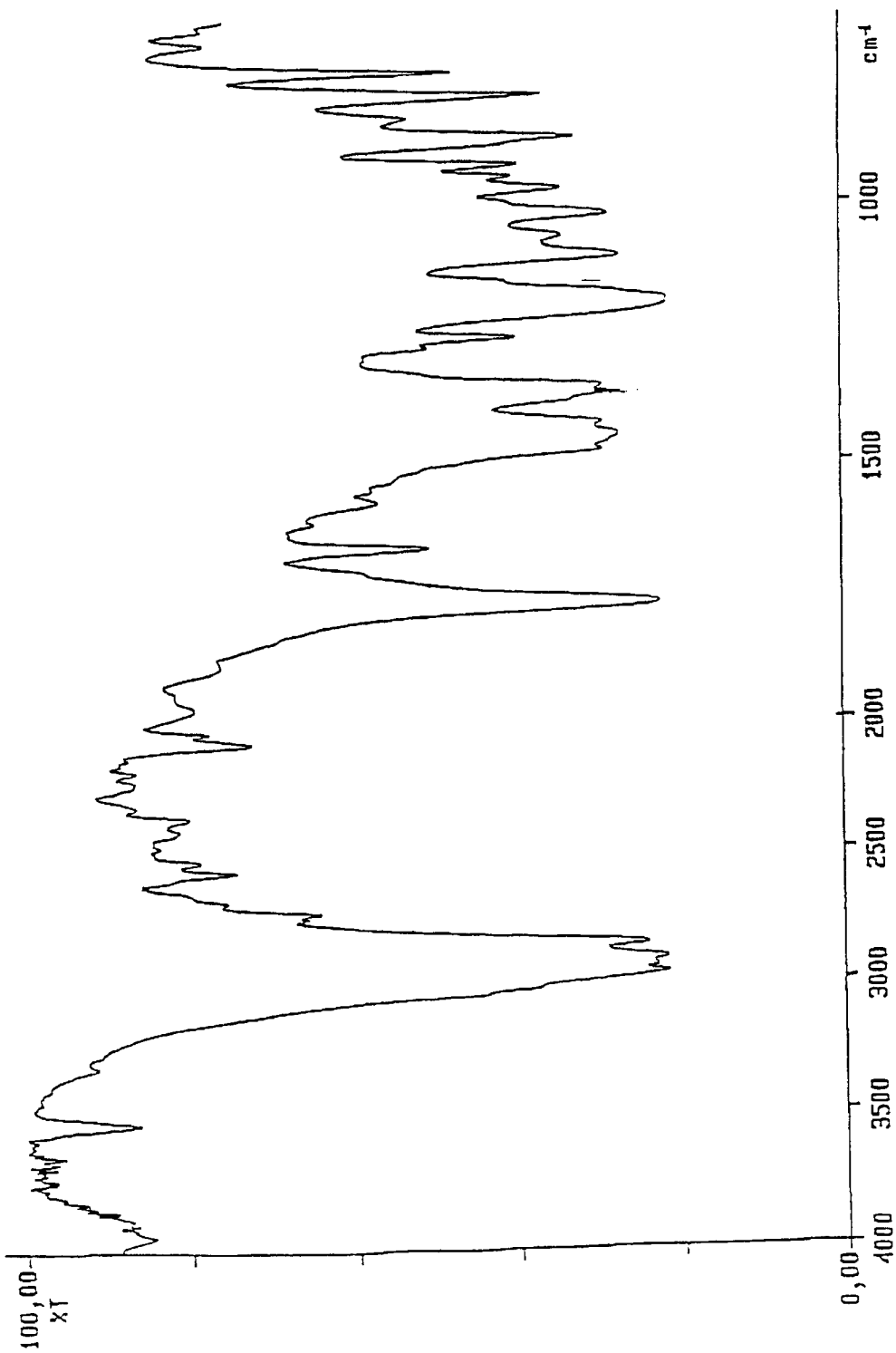
FIG. 1 represents the infrared spectrum of ubiquinole diacetate.

Particularly preferred among the compounds of formula I in which X=CO, are the compounds in which R is linear $C_1$–$C_6$ alkyl, in particular methyl, propyl and ethyl. Particularly preferred compounds are ubiquinole diacetate and dipropionate.

Particularly preferred among the compounds of formula I in which X is absent, are the compounds in which R is linear $C_1$–$C_6$ alkyl, in particular the compounds in which R is methyl, propyl and ethyl. Particularly preferred compounds are ubiquinole diethylether and dimethylether.

The compounds of formula I can be prepared according to the following synthesis, which are therefore a further object of the present invention.

Synthesis of the compounds of formula I in which X=CO can take place according to the synthetic scheme (a) by reacting the coenzyme $Q_{10}$ with an anhydride or according to the synthetic scheme (b), in which in a first stage the coenzyme $Q_{10}$ is reacted with a reducing agent and in a second stage the ubiquinole obtained is reacted with an acylic chloride. The reaction schemes are as follows:

a) $CoQ_{10}+(RCO)_2O \rightarrow$ compounds of formula I in which X=CO the reaction is carried out in an acid environment in the presence of metallic zinc and in an organic solvent;

$b_1$) $CoQ_{10}+NaBH_4$ in organic solvent $\rightarrow CoQ_{10}H_2$ $b_2$) $CoQ_{10}H_2+RCOCl$ in organic solvent $\rightarrow$ compounds of formula I in which X=CO.

Synthesis of the compounds of formula I in which X is absent.

Synthesis of compounds of formula I in which X is absent can be done according to the synthetic scheme (c), reacting the coenzyme $Q_{10}$ with a dialkylic sulphate or according to the synthetic scheme (d) in which in a first stage the coenzyme $Q_{10}$ is reduced to ubiquinole by effect of a reducing agent and in a second stage the ubiquinole obtained is reacted with an iodoalcane.

The reaction schemes are as follows:

c) $CoQ_{10}+(RO)_2SO_2 \rightarrow$ compounds of formula I in which X is absent, the reaction is carried out in an organic solvent in a basic environment, preferably in a Lewis base.

$d_1$) $CoQ_{10}+NaBH_4 \rightarrow CoQ_{10}H_2$ $d_2$) $CoQ_{10}H_2+IR \rightarrow$ compounds of formula I in which X is absent.

In the preceding schemes $NaBH_4$ is preferably used as a Lewis base, as it also supplies the reducing activity in case of synthesis b1) and d1), and IR indicates iodoalcane, R has the meaning indicated in formula I.

For preference, the following reaction solvents are used: hexane, tetrahydrofuran, methanol.

The compounds of formula I according to the invention can be used as active therapeutic agents with the aim of obtaining the necessary integration of ubiquinole in those cases in which a low level has been found in the tissues, as within the organism under the action of the esterases (in the case of compounds of formula I in which X=CO) or of microsomial enzymes (in the case of compounds of formula I in which X is absent) ubiquinole is freed respectively as a result of hydrolysis or of dealkylation of the compounds of formula I.

It should be underlined that following the administration of active therapeutic agents containing compounds of formula I the bioavailability of ubiquinole increases, as hydrolysis of the compounds of formula I according to the present invention (which as said produces ubiquinole) does not take place due to the action of the quinone-reductases, which are notoriously low in level in all organisms suffering from oxidative cellular stress, but on the contrary takes place due to the action of the esterases or of the microsomial enzymes.

A further object of the present invention are therefore active therapeutic agents comprising one or more compounds of formula I.

The active therapeutic agents according to the present invention can be used in treatment of all the affections and diseases of the organism that involve or can be traced to continuous or high intracellular oxidative stress, such as for example that arising in cases of aged organisms or ones in which there is incorrect functioning of the biological reducing function in electron carrier systems.

In particular the active therapeutic agents according to the present invention can also be used for treatment of AIDS, tuberculosis, leprosy.

A further object of the present invention are pharmaceutical formulations containing a pharmacologically effective amount of one or more compounds of formula I in addition to other active principles, additives and/or pharmaceutically tolerable vehicles. Among the other active principles it is possible to mention Vitamin E acetate, selenium, methionin.

In case of administration of ubiquinole derivatives, amounts of between 50 and 200 mg/die are preferred.

The following is a pharmaceutical formulation in the form of a pill:

|  | Amount | Percentage by weight |
|---|---|---|
| Ubiquinole Q10 acetate | 58.440 mg | 14.610% |
| Orange flavouring, powder | 4.000 mg | 1.000% |
| Cellulose | 60.000 mg | 15.000% |
| Lactose | 267.160 mg | 66.790% |
| Colloidal silica | 4.000 mg | 1.000% |
| Sodium saccarinate | 0.400 mg | 0.100% |
| Mg Stearate | 6.000 mg | 1.500% |
| Total | 400.000 mg | 100.00% |

The following are examples of production for compounds of formula I.

EXAMPLE 1

Production of Ubiquinole Diacetate

In a 500 ml flask fitted with a serpentine condenser and a mixer, 10 g of oxidised ubiquinone are suspended in 30 ml of hexane; 30 ml of ultrapure acetic anhydride, 10 grams of powdered zinc and 2 grams of powder of anhydrous sodium acetate form are added.

The mixture is heated slightly under stirring until the yellow-orange colour of the hexane-phase ubiquinone completely disappears; the mixture is then brought to the boiling point for 2–3 minutes.

25 ml of glacial acetic acid are added and the mixture is brought to boiling point to dissolve the product and part of the precipitated zinc acetate.

The solution is decanted while hot from the zinc acetate and from the zinc, which are washed with acetic acid (10 ml) and hexane (50 ml). The acetic-hexanic solutions are collected in another flask and distilled water (approximately 100 ml) is gradually added to hydrolyse the remaining acetic anhydride.

When bubbling ceases, the hexane phase is separated off using a separator funnel, and washed 3 times with 20 ml of distilled water.

The hexane is distilled off and, in the residue, very pure ubiquinole diacetate is obtained (percentage yield: 95%).

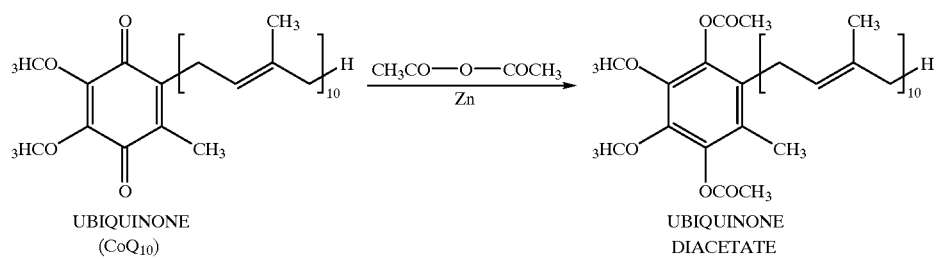

UBIQUINONE (CoQ$_{10}$)     UBIQUINONE DIACETATE

EXAMPLE 2

Preparation of Ubiquinole Dimethylether

Equip a four-necked 500 ml flask with a separator funnel, a mechanical mixer, a reflux condenser and a thermometer. There must also be a continuous flow of nitrogen into the flask through one neck, to prevent oxidation by atmospheric oxygen. (Alternatively, the apparatus can be protected against oxidation using a Bunsen valve applied to the reflux condenser). The funnel is filled with 5 ml (6.7 g) of dimethyl sulphate, which are added to the mixture drop by drop over a period of approximately 30 minutes, under energetic stirring. Methylation is completed by reflux heating for approximately 2 hours, during which time 30–50 ml of hexane can be added through the separator funnel, which previously contained the dimethylsulphate. During heating, any dimethylsulphate that has not reacted will be destroyed.

The mixture is allowed to cool, acidified with diluted sulphuric acid and transferred to a separator funnel. The lower phase is eliminated and the hexane phase is washed twice with diluted sulphuric acid and then with water until acidity disappears.

The hexane phase is dried on anhydrous sodium or magnesium sulphate and then the hexane is distilled (percentage yield: 85%).

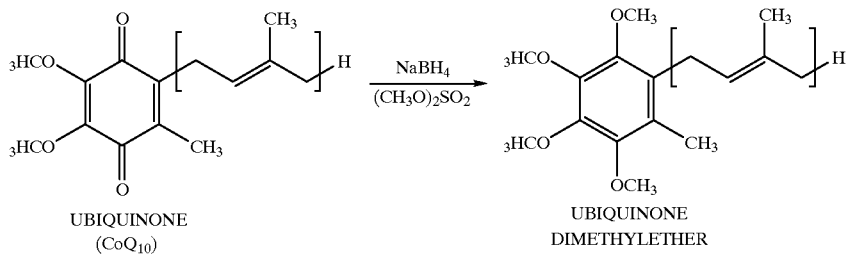

The following tables show, as a non-limiting example, some compounds of formula I that can be obtained using the various reaction schemes. The chemical and physical data relate to the product obtained; the UV spectra have been recorded with the compounds dissolved in hexane; the infra-red spectrums of the ethers have been recorded on NaCl crystals, those of the esters on KBr pastilles.

TABLE 1

(Products obtained according to scheme a)

| Anhydride used | Product obtained | R in formula I |
|---|---|---|
| Acetic anhydride | Ubiquinole diacetate | —CO—CH$_3$ |

Figure 2:
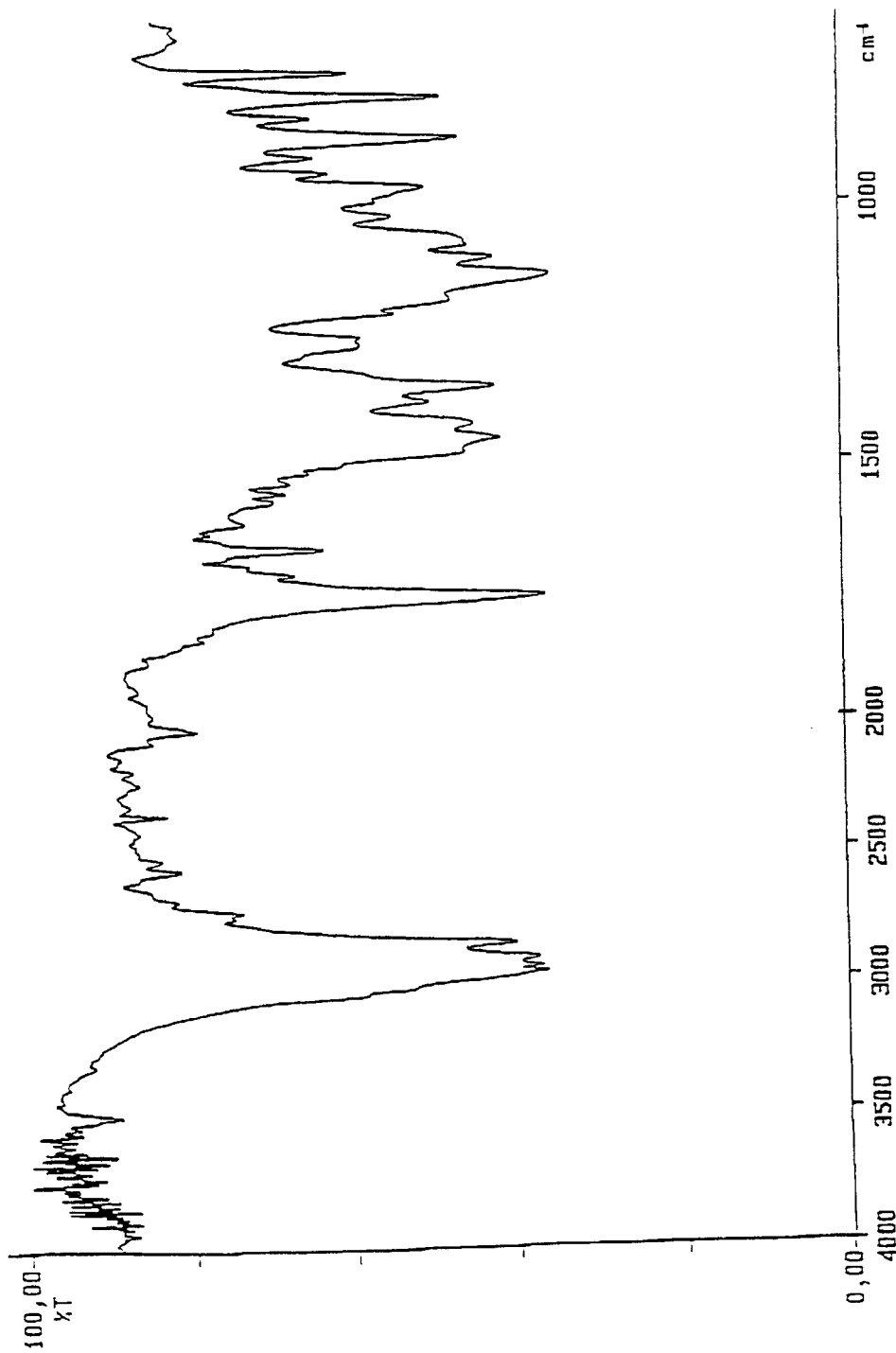
FIG. 2 represents the infrared spectrum of ubiquinole dipropionate.
Figure 3:
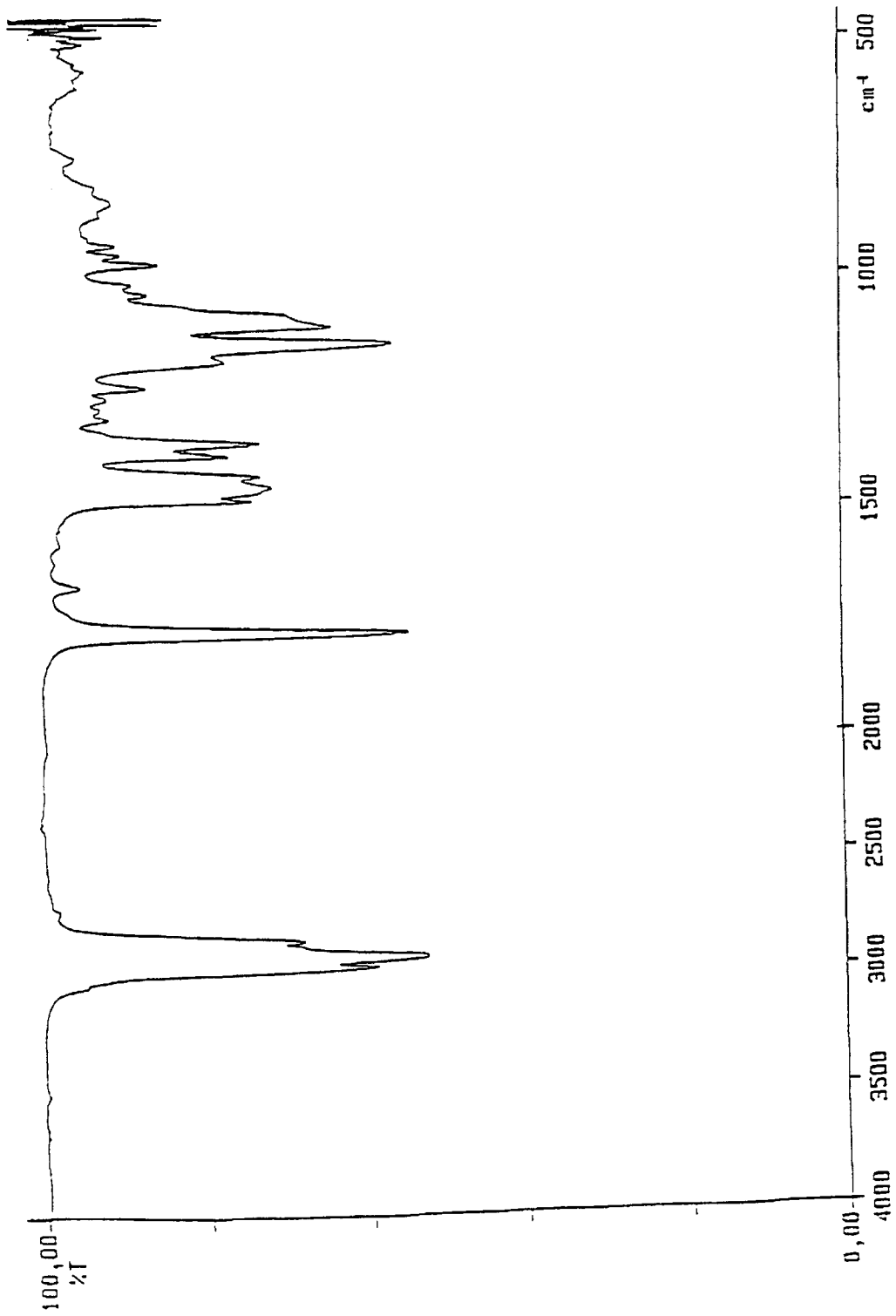
FIG. 3 represents the infrared spectrum of ubiquinole dibutyrrhate.

Chemical/physical data: MW 949.4; UV spectrum (maximum absorption at 268.5 nm, minimum at 250.5 nm) the infra-red spectrum is reported in FIG. 1.
Propionic anhydride Ubiquinole dipropionate —CO—CH$_2$—CH$_3$
Chemical/physical data: MW 977.4; UV spectrum (maximum absorption at 268.5 nm, minimum at 250.5 nm) the infra-red spectrum is reported in FIG. 2.
Butyric anhydride Ubiquinole dibutyrrate —CO—(CH$_2$)$_2$—CH$_3$
Chemical/physical data: MW 1005.4; UV spectrum (maximum absorption at 268.5 nm, minimum at 250.5 nm) the infra-red spectrum is reported in FIG. 3.

Similar results can be obtained using the synthesis scheme b.

TABLE 2

(Products obtained according to scheme c)

Figure 4:
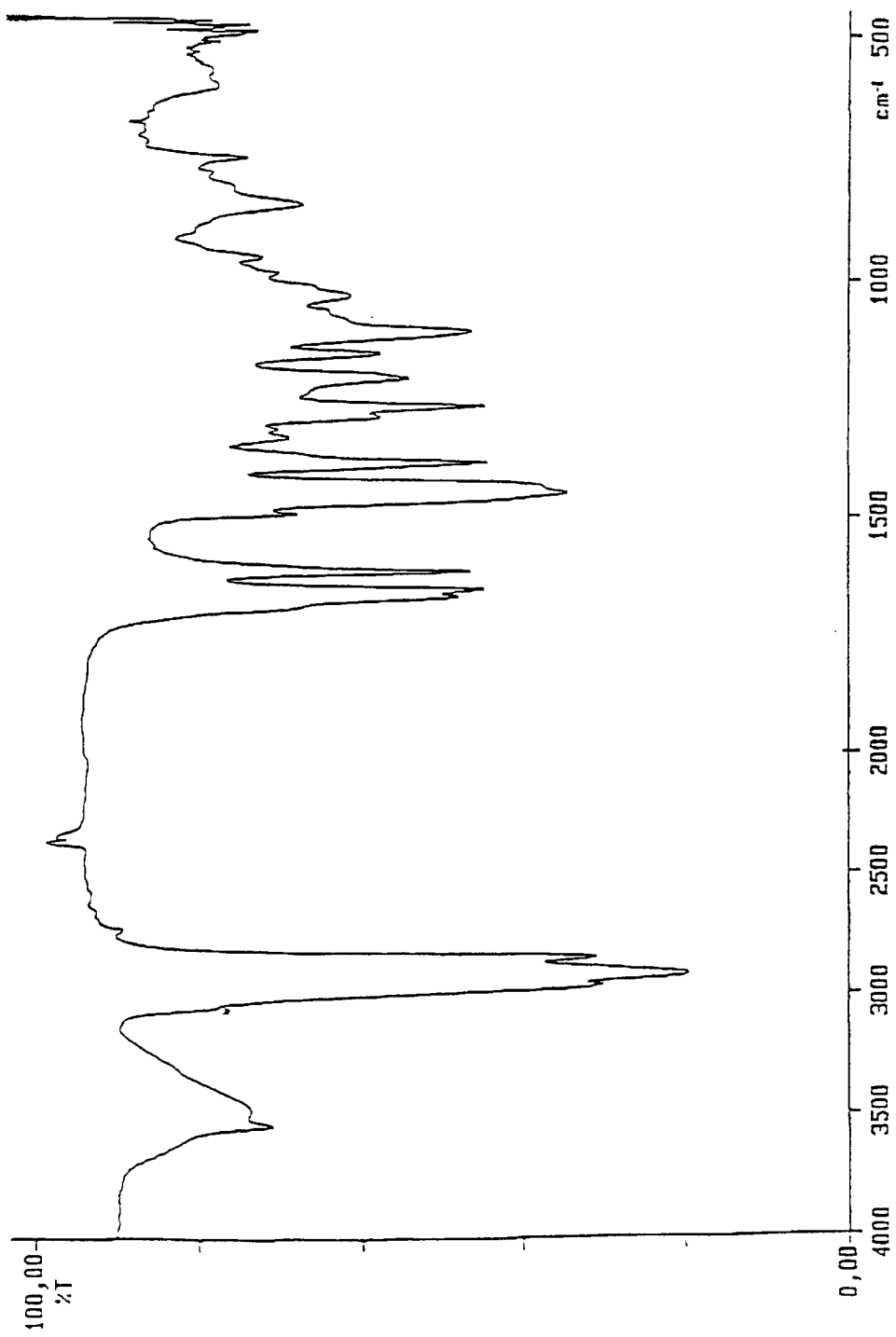
FIG. 4 represents the infrared spectrum of ubiquinole dimethylether.

| Alkylating agent | Product obtained | R in formula I |
|---|---|---|
| Dimethylsulphate | Ubiquinole dimethylether | —CH$_3$ |
| Chemical/physical data: MW 893.4; UV spectrum (maximum absorption at 274.5 nm, minimum at 236.5 nm) the infra-red spectrum is reported in FIG. 4. | | |
| Diethylsulphate | Ubiquinole diethylether | —CH$_2$—CH$_3$ |

Figure 5:
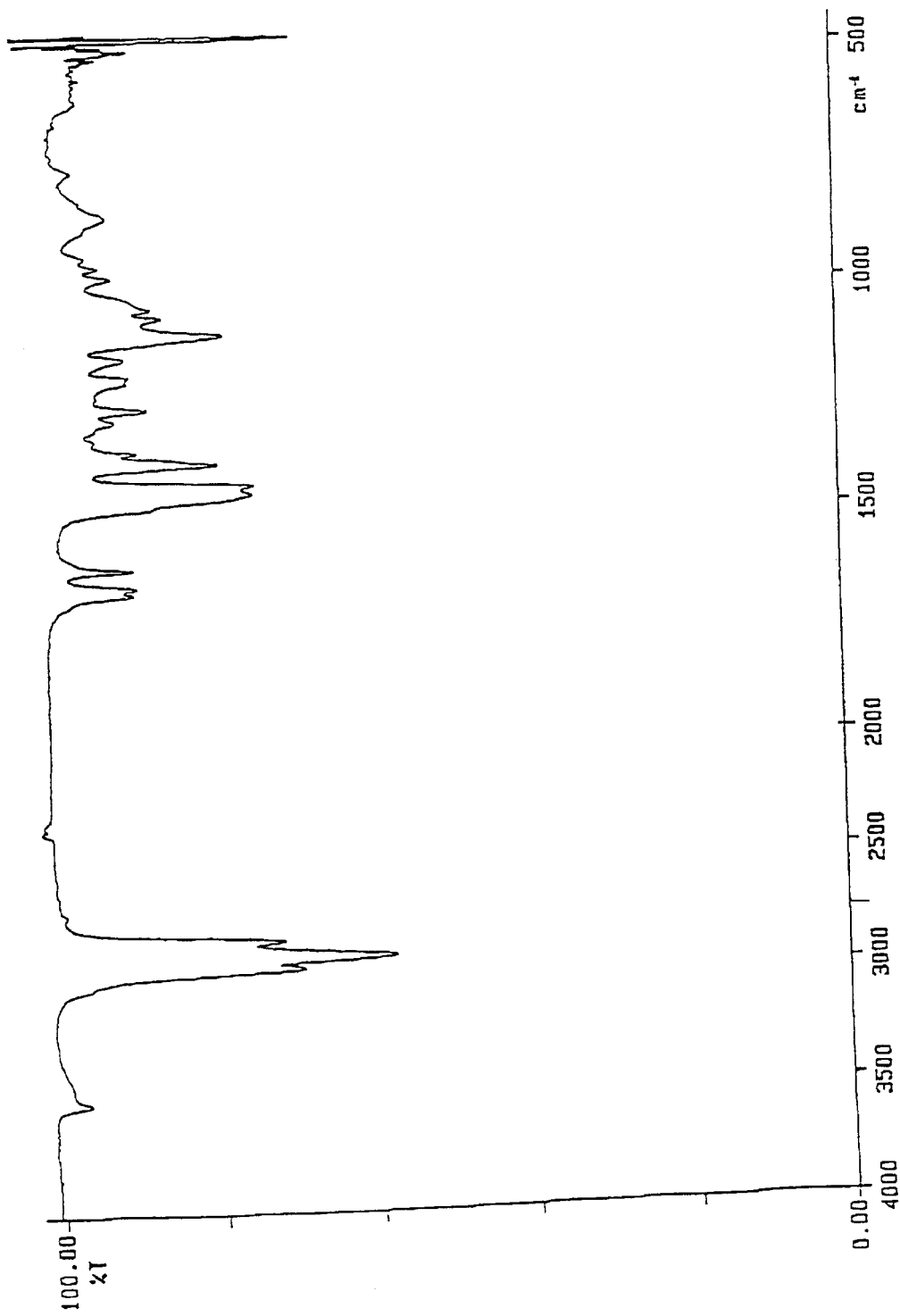
FIG. 5 represents the infrared spectrum of ubiquinole diethylether.

Chemical/physical data: MW 921.4; UV spectrum (maximum absorption at 274.5 nm, minimum at 236.5 nm) the infra-red spectrum is reported in FIG. 5.

Similar results can be obtained using the reaction scheme d.

The present invention has been described in detail with reference to examples of preparation, but it will be understood that variations and modifications may be made by a person skilled in the art without departing from the scope of protection of the present industrial privilege.

What is claimed is:

1. A method for the treatment of intracellular oxidative stress in a patient in need thereof, comprising administering to said subject a therapeutically effective amount of at least one compound of formula I

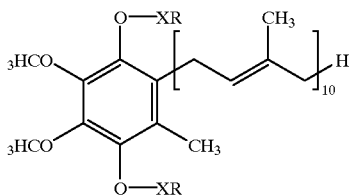

in which X is absent or a CO group,
R is a linear or branched alkyl group with a number of carbon atoms from 1 to 20 or an arylic group, optionally substituted with a C$_1$–C$_6$ alkylic substituent.

2. The method according to claim 1, wherein in the compound of formula 1, X is CO.

3. The method according to claim 1, wherein, in the compound of formula 1, X is absent.

4. The method according to claim 2, wherein, in the compound of formula 1, R is linear or branched alkyl of 1 to 6 carbons.

5. The method according to claim 4, wherein in the compound of formula 1, R is methyl, ethyl or propyl.

6. The method according to claim 5, wherein the compound of formula 1 is ubiquinole diacetate.

7. The method according to claim 5, wherein the compound of formula 1 is ubiquinole dipropionate.

8. The method according to claim 5, wherein the compound of formula 1 is ubiquinole dibutyerate.

9. The method according to claim 3, wherein in the compound of formula 1, R$_1$ is a linear or branched alkyl of 1 to 6 carbons.

10. The method according to claim 9, wherein in the compounds of formula 1, R is methyl, ethyl or propyl.

11. The method according to claim 10, wherein the compound of formula 1 is ubiquinole dimethylether.

12. The method according to claim 11, wherein the compound of formula 1 is ubiquinole diethylether.

13. The method as claimed in claim 1, for the treatment of a condition of tuberculosis, leprosy or AIDS, wherein said subject is suffering from a said condition.

14. The method of claim 1, wherein said compound is ubiquinile diacetate, ubiquinole dipropionate, ubiquinole dibutyerate, ubiqionole dimethylether or ubiquinole diethylether.

15. Pharmaceutical composition comprising a therapeutically effective amount of one or more of the compounds of formula I, together with an additive or a pharmaceutically tolerable vehicle.

16. Pharmaceutical composition according to claim 14, further containing one or more additional active principles.

17. A process for the production of a compound as defined in claim 2, in which the ubiquinone is reacted with an anhydride of formula $(RCO)_2O$ in an organic solvent, in the presence of zinc and in an acid environment.

18. A process for the production of a compound as defined in claim 2, in which in a first stage the ubiquinone is reacted with a reducing agent in an organic solvent and in a second stage the ubiquinole obtained is reacted with an acid chloride of formula RCOCl.

19. A process for the production of a compound as defined in claim 3, in which the ubiquinone is reacted with a dialkylic or diarylic sulphate of formula $(RO)_2SO_2$ in an organic solvent and in a basic environment for the presence of $NaBH_4$.

20. A process for the production of a compound as defined in claim 3, in which in a first stage the ubiquinone is reacted with $NaBH_4$ in an organic solvent to obtain ubiquinole, which in a second stage is reacted with an iodoalkane of formula IR.

* * * * *